United States Patent [19]

Klar et al.

[11] Patent Number: 5,376,683
[45] Date of Patent: Dec. 27, 1994

[54] Δ8- AND Δ9-PROSTAGLANDIN DERIVATIVES, PROCESS FOR THEIR PRODUCTION AND THEIR PHARMACEUTICAL USE

[75] Inventors: Ulrich Klar; Hartmut Rehwinkel; Helmut Vorbrüggen; Karl H. Thierauch; Claus S. Stürzebecher, all of Berlin, Germany

[73] Assignee: Schering Aktiengesellschaft, Berlin and Bergkamen, Germany

[21] Appl. No.: 982,111

[22] Filed: Nov. 25, 1992

Related U.S. Application Data

[63] Continuation of Ser. No. 679,057, May 6, 1992, abandoned.

[30] Foreign Application Priority Data

Jul. 14, 1989 [DE] Germany .................. 3923798

[51] Int. Cl.$^5$ .................. C07C 405/00; A61K 31/557
[52] U.S. Cl. .................. 514/530; 514/570; 548/237; 549/371; 560/60; 560/61; 562/470; 562/471
[58] Field of Search .................. 560/60, 61; 562/470, 562/471; 548/237; 544/374; 514/530, 570

[56] References Cited

PUBLICATIONS

Olah, George A. et al., "Synthetic Methods and Reactions IX$^1$ Fluorination of Secondary- and Tertiary-Alcohols with Polyhydrogen Fluoride/Pyridine (Trialkylamine) Reagents."
J. of American Chem. Society Feb. 6, 1974, "Synthetic Methods and Reactions . . . " pp. 925–927.
Green, Chem Comm 611 (1977).
Somekh, JOC. 48 907 (1983).

Primary Examiner—Robert Gerstl
Attorney, Agent, or Firm—Millen, White, Zelano & Branigan

[57] ABSTRACT

The invention relates to Δ$^8$- and Δ$^9$-prostaglandin derivatives of formula I,

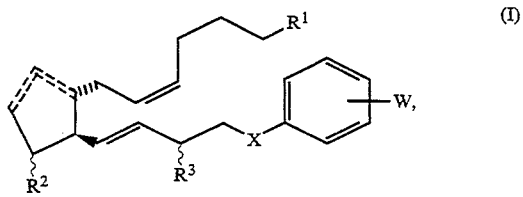

in which $\frown$ means the radicals $\frown$ or $\frown$,
R$^1$ means

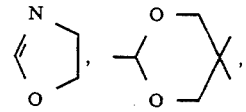

COOR$^4$ or CONHR$^5$,
R$^2$ and R$^3$ respectively mean a hydrogen atom or a hydroxy group, and the OH group can be respectively in alpha- or beta- position,
means a CH$_2$ group, an O or S atom,
W means hydrogen, —OR$^6$, halogen, —CN—, —NO$_2$, trifluoromethyl or COOR$^6$, and if R$^4$ means hydrogen, their salts with physiologically compatible bases, the alpha-, beta- or gamma- cyclodextrin clathrates, as well as the compounds of formula I encapsulated with liposomes, process for their production and their pharmaceutical use.

5 Claims, No Drawings

Δ8- AND Δ9-PROSTAGLANDIN DERIVATIVES, PROCESS FOR THEIR PRODUCTION AND THEIR PHARMACEUTICAL USE

This application is a continuation of application Ser. No. 07/679,057, filed May 6, 1991, now abandoned.

The invention relates to Δ8- and Δ9-prostaglandin derivatives, process for their production as well as their use as auxiliary agents for pharmacological studies and as pharmaceutical agents.

It has been found, surprisingly, that chemically and metabolically stable prostaglandin analogs, whose pharmacological properties are comparable to those of unstable thromboxane $A_2(TXA_2)$ or $PGH_2$, are obtained by the introduction of a double bond in 8 or 9 position in connection with an aromatic substituent on 17 position.

The compounds of this invention therefore are suitable as auxiliary agents for pharmacological characterizations as well as for selective treatment of diseases, which are attributable to a deficiency of endogenous $TXA_2/PGH_2$.

The invention relates to Δ8- and Δ9-prostaglandin derivatives of formula I,

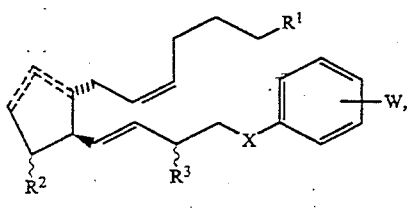

in which ⌢ means the radicals ⌢ or ⌢, $R^1$ means

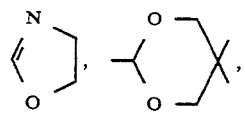

$COOR^4$, in which $R^4$ can mean hydrogen or a $C_1$-$C_{10}$ alkyl radical optionally substituted by halogen, phenyl, $C_1$-$C_4$ alkoxy or di-($C_1$-$C_4$) alkylamino, a $C_3$-$C_{10}$ cycloalkyl radical, a $C_7$-$C_{16}$ aralkyl radical, a phenacyl radical substituted by W, a $C_6$-$C_{12}$ aryl radical or a 5- or 6-member heterocyclic radical with at least one N, O or S atom, or $R^1$ can be a $CONHR^5$ radical with $R^5$ meaning hydrogen, $C_1$-$C_{10}$ alkanoyl or $C_1$-$C_{10}$ alkanesulfonyl, $R^2$ and $R^3$ respectively mean a hydrogen atom or a free or functionally modified hydroxy group, in which the OH group can be respectively in alpha- or beta-position, X means a $CH_2$ group, an O or S atom, W means hydrogen, —$OR^6$, halogen, —CN—, —$NO_2$, trifluoromethyl or $COOR^6$, $R^6$ can be hydrogen, $C_1$-$C_{10}$ alkyl, $C_6$-$C_{12}$ aryl or $C_7$-$C_{16}$ aralkyl substituted by halogen, and, if $R^4$ means hydrogen, their salts with physiologically compatible bases, as well as the alpha-, beta- or gamma-cyclodextrin clathrates, as well as the compounds of formula I encapsulated with liposomes.

The definition of 5- or 6-membered heterocyclic radical relates to heterocycles, which contain at least one heteroatom, preferably nitrogen, oxygen or sulfur. For example, there can be mentioned 2-furyl, 3-furyl, 2-thienyl, 3-thienyl, 2-pyridyl, 3-pyridyl, 4-pyridyl.

As alkyl groups $R^4$ and $R^6$, straight-chain or branched-chain alkyl groups with 1–10 C atoms, such as, for example, methyl, ethyl, propyl, isopropyl, butyl, isobutyl, tert-butyl, pentyl, isopentyl, neopentyl, heptyl, hexyl, decyl, are suitable.

Alkyl groups $R^4$ and $R^6$ can be substituted by halogen atoms, hydroxy groups, $C_1$-$C_4$ alkoxy groups, $C_6$-$C_{12}$ aryl groups, which can be substituted by halogen, di-($C_1$-$C_4$)-alkylamines and tri-($C_1$-$C_4$)-alkylammonium. Those alkyl groups which are singly substituted are preferred.

As substituents, for example, there can be mentioned fluorine, chlorine or bromine atoms, phenyl, dimethylamino, diethylamino, methoxy, ethoxy.

As preferred alkyl groups $R^4$ and $R^6$, those with 1–4 C atoms, such as, for example, methyl, ethyl, propyl, isobutyl, butyl, can be mentioned.

As aryl groups $R^4$ and $R^6$, for example, phenyl, diphenyl, 1-naphthyl and 2-naphthyl, which can be substituted by 1–3 halogen atoms, a phenyl group, 1–3 alkyl groups each with 1–4 C atoms, a chloromethyl group, fluoromethyl group, carboxyl group, $C_1$-$C_4$ alkoxy group or hydroxy group, are suitable. The substitution in 3- and 4-position on the phenyl ring is preferred, for example, by fluorine, chlorine, $C_1$-$C_4$ alkoxy or trifluoromethyl or in 4-position by hydroxy.

Cycloalkyl groups $R^4$ can contain 3–10 carbon atoms, preferably 3–6 carbon atoms, in the ring. The rings can be substituted by alkyl groups with 1–4 carbon atoms. For example, there can be mentioned cyclopropyl, cyclobutyl, cyclopentyl, methylcyclopentyl, methylcyclohexyl.

Especially preferred cycloalkyl groups are cyclopentyl and cyclohexyl.

As $C_7$-$C_{16}$ aralkyl, the following radicals are meant: phenylsubstituted alkyl radicals (straight-chain and branched) with 1–10 C atoms, such as, for example, benzyl, phenylmethyl, alphaphenylethyl, 3-phenylpropyl, etc. But as Ar, 1- or 2-naphthyl with a suitably shorter alkyl chain are also suitable.

The alkyl groups or alkoxy groups with 1–4 C atoms mentioned as substituents should be straight-chain or branched-chain.

The hydroxy groups in $R^2$ and $R^3$ can be functionally modified, for example, by etherification or esterification, and the free or modified hydroxy groups can be in alpha- or beta-position, and free hydroxy groups are preferred.

As ether and acyl radicals, the radicals known to one skilled in the art are suitable. Easily cleavable ether radicals, such as, for example, the tetrahydropyranyl radical, tetrahydrofuranyl radical, tert-butyldimethylsilyl radical, tertbutyldiphenylsilyl radical, tribenzylsilyl radical, are preferred. As acyl radicals, for example, acetyl, propionyl, butyryl, benzoyl are suitable.

Halogen in the definitions for $R^4$, $R^6$ and W means fluorine, chlorine and bromine.

Radicals "$C_1$-$C_{10}$ alkanoyl" or "$C_1$-$C_{10}$-alkanesulfonyl" for $R^5$ correspond to the already mentioned alkyl groups of the same length with the difference that they are bound on a carboxyl group. $C_1$-$C_4$ alkanoyl or $C_1$-$C_4$ alkanesulfonyl are preferred.

Inorganic and organic bases are suitable for salt formation with the free acids ($R^4$=H), as they are known to one skilled in the art for forming physiologically compatible salts. For example, there can be mentioned: alkali hydroxides, such as sodium hydroxide or potassium hydroxide, alkaline earth hydroxides, such as calcium hydroxide, ammonia, amines, such as ethanolamine, diethanolamine, triethanolamine, n-methylglucamine, morpholine, tris-(hydroxymethyl)methylamine, etc.

Preferred compounds of formula I are compounds in which $\underset{\frown}{\frown}$ means the radicals $\underset{\frown}{\frown}$ $R^1$ means the group $COOR^4$,
$R^2$ means hydrogen or hydroxyl,
$R^3$ means hydrogen or hydroxyl,
$R^4$ means hydrogen or $C_1$–$C_6$ alkyl,
$R^5$ means methanesulfonyl,
X means oxygen or $CH_2$,
W means hydrogen or fluorine.

The invention further relates to a process for the production of compounds of formula I, which is characterized in that a compound of formula II

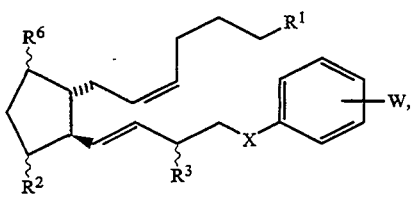

(II)

in which
$R^4$ means a hydroxy group and $R^1$, $R^2$, $R^3$, X and W have the above-indicated meanings and free OH groups in $R^2$, $R^3$ and W are protected, is reacted with diethylaminosulfur trifluoride [M. Sharma, Tetrahedron Lett. 573 (1977); W. J. Middleton, J. Org. Chem. 40, 574 (1975)] or other fluorinating agents, such as, e.g., $(HF)_n$-pyridine [G. A. Olah, Synthesis 786 (1973)] or $SeF_4$-pyridine [G. A. Olah, J. Am. Chem. Soc. 96, 925 (1974)] and optionally protected hydroxy groups in $R^2$, $R^3$ and W are released and/or free hydroxy groups are esterified, etherified, and/or an esterified carboxy group is saponified or a carboxy group with a physiologically compatible base is converted to a salt or reacted to a clathrate with alpha-, beta- or gamma-cyclodextrin or encapsulated with liposomes.

The reaction of the compounds of the general formula II to the compounds of the general formula I is performed with diethylaminosulfur trifluoride at −80° C. to +40° C., preferably at −70° C. to +25° C. As a solvent, dichloromethane, 1.1.2-trifluorotrichloroethane, pyridine, toluene, benzene, ethylene chloride, i.a., preferably toluene and pyridine, are suitable.

The release of functionally modified hydroxy groups $R^2$, $R^3$ and W takes place according to the methods known to one skilled in the art. For example, the cleavage of the ether protecting groups is performed in an aqueous solution of an organic acid, such as, e.g., acetic acid, propionic acid, citric acid, i.a., or in an aqueous solution of an inorganic acid, such as, e.g., hydrochloric acid, or in the case of tetrahydropyranyl ethers with-use of Pyridinium-p-toluenesulfonate, preferably in alcohols as solvent or with use of anhydrous magnesium bromide, preferably in diethyl ether as a solvent.

To improve the solubility, a water-miscible inert solvent is suitably added with use of aqueous-acid reaction conditions. Proven as suitable, there are, e.g., alcohols, such as methanol and ethanol, ethers, such as dimethoxyethane, dioxane and tetrahydrofuran, and tetrahydrofuran is preferably used.

The cleavage of silylether protecting groups takes place, for example, with tetrabutylammonium fluoride according to the methods known to one skilled in the art. As solvent, for example, tetrahydrofuran, diethyl ether, dioxane, methylene chloride, etc., are suitable. The cleavage is performed preferably at temperatures between 20° and 80° C.

The saponification of the acyl groups and prostaglandin ester is performed according to the methods known to one skilled in the art, such as, for example, with basic catalysts, such as, e.g., with alkali or alkaline-earth carbonates or hydroxides in an alcohol or the aqueous solution of an alcohol. As alcohols, aliphatic alcohols, such as, e.g., methanol, ethanol, butanol, etc., but preferably methanol, are suitable. As alkali carbonates and alkali hydroxides, there can be mentioned lithium, sodium and potassium salts. The lithium and potassium salts are preferred. As alkaline-earth carbonates and alkaline-earth hydroxides, for example, calcium carbonate, calcium hydroxide and barium carbonate are suitable. The reaction generally takes place at −10° to +70° C., but preferably at +25° C.

The introduction of the ester groups $CO_2R^4$ for $R^1$ or $CO_2R^6$ for W, in which $R^4$ or $R^6$ represents an alkyl group with 1–10 C atoms, takes place according to the methods known to one skilled in the art. The 1-carboxy compounds ($R^4$=H or $R^6$=H) are reacted, for example, with diazohydrocarbons in a way known in the art. The esterification with diazohydrocarbons takes place, e.g., in that a solution of the diazohydrocarbon in an inert solvent, preferably in diethyl ether, is mixed with the 1-carboxy compound, dissolved in the same or in another inert solvent, such as, e.g., methylene chloride. After completion of the reaction within 1 to 60 minutes, the solvent is removed and the ester is purified in the usual way. Diazoalkanes are either known or can be produced according to known methods (Org. Reactions, Vol. 8, pages 389–394 (1954)).

The introduction of the ester group $CO_2R^4$ for $R^1$ or $CO_2R^6$ for W, in which $R^4$ or $R^6$ represents a substituted or an unsubstituted aryl group, takes place according to the methods known to one skilled in the art. For example, the 1-carboxy compounds are reacted with the corresponding arylhydroxy compounds with dicyclohexylcarbodiimide in the presence of a suitable base, such as, e.g., pyridine, dimethylaminopyridine, triethylamine, in an inert solvent, such as, e.g., methylene chloride, ethylene chloride, chloroform, ethyl acetate, tetrahydrofuran, but preferably with chloroform. The reaction is performed at temperatures between −30° C. and +50° C., preferably at +10° C.

The prostaglandin derivatives of formula I with $R^4$ or $R^6$ meaning a hydrogen atom can be converted to salts with suitable amounts of the corresponding inorganic bases with neutralization. For example, by dissolving the corresponding prostaglandin acids in water, which contains stoichiometric amounts of the base, the solid inorganic salt is obtained after evaporation of the water or after addition of a water-miscible solvent, e.g., alcohol or acetone.

The production of the amine salts takes place in the usual way. For this purpose, the prostaglandin acid is dissolved in a suitable solvent, such as, e.g., ethanol, acetone, diethyl ether or benzene and 1 to 5 equivalents of the respective amine of this solution is added. In this case, the salt usually accumulates in solid form or is isolated in the usual way after the evaporation of the solvent.

The functional modification of the free hydroxy groups takes place according to the methods known to one skilled in the art. For the introduction of the ester protecting groups, it is reacted, for example, with dihydropyran or methyl vinyl ether in methylene chloride or chloroform with use of catalytic amounts of an acidic condensing agent, such as, e.g., toluenesulfonic acid. The respective enol ether is added in excess, preferably in 1.2 to 10 times the amount of the theoretical requirement. The reaction normally takes place at $-10°$ C. to $+30°$ C. and is completed after 2 to 45 minutes.

For the introduction of silylether protecting groups, it is reacted, for example, with t-butyl-diphenylchlorosilane or t-butyl-dimethylchlorosilane in dimethylformamide with use of a base such as, e.g., imidazole. The respective silyl chloride is added in excess, preferably in 1.05 to 4 times the amount of the theoretical requirement. The reaction normally takes place at $0°$ C. to $30°$ C. and is completed after 1 to 24 hours.

The introduction of the acyl protecting groups takes place by a compound of formula I being reacted in a way known in the art with a carboxylic acid derivative, such as, e.g., acid chloride, acid anhydride, etc.

The new chemically and metabolically stable $\Delta^8$- and $\Delta^9$-fluoroprostaglandin derivatives have pharmacological properties which are comparable to those of the unstable thromboxane $A_2(TXA_2)$ or $PGH_2$. As $TXA_2/PGH_2$ receptor agonists, they thus represent a valuable diagnostic instrument for characterizing prostaglandin receptors or $TXA_2/PGH_2$ receptor subtypes, with which the importance of the $TXA_2/PGH_2$-dependent stimulation of platelets and vessels can be established. This applies both for in vitro tests, such as, e.g., receptor characterization or displacement on the receptor, platelet aggregation inhibition tests, vessel layer constriction, etc., and for pharmacological studies on the animal.

The $TXA_2/PGH_2$ receptor agonists can be used for specific weakening or elimination of the action of cyclooxygenase inhibitors, of $TXA_2$-synthetase inhibitors as well as of $TXA_2/PGH_2$ receptor blockers. Another possibility of use exists in the partial downward adjustment of the $TXA_2/PGH_2$ action in clinical pictures with increased sensitivity to, or production of, thromboxane, such as, e.g., those of coronary arteries or vessels with arteriosclerotic lesions.

In combination with a $TXA_2/PGH_2$ receptor antagonist, the $TXA_2/PGH_2$ receptor agonist can be used for diagnostic clarification of the involvement of $TXA_2/PGH_2$-dependent processes in such clinical pictures which require no systemic dose of a $TXA_2/PGH_2$ receptor agonist for this diagnosis but also in other clinical pictures, provided that undesirable effects of the $TXA_2/PGH_2$ receptor agonist can be counteracted by an antagonist.

The $TXA_2/PGH_2$ receptor agonists are further suitable for local control of hemorrhage in the case of defects of the platelet function, which are based on an impairment of the $TXA_2/PGH_2$ formation and/or action.

The $\Delta^8$- and $\Delta^9$-prostaglandin derivatives of this invention can also be used in combination, e.g., with beta-blockers, diuretics, phosphodiesterase inhibitors, Ca antagonists or nonsteroidal antiinflammatory agents.

The dose of the compounds is 1–1000 micrograms/kg/per day, if it is administered to the human patient. The unit dose for the pharmaceutically acceptable vehicle is 10 micrograms to 100 micrograms.

For parenteral administration, sterile, injectable aqueous or oily solutions are used. For oral administration, for example, tablets, coated tablets or capsules are suitable. The invention thus also relates to pharmaceutical agents based on the compounds of formula I and usual auxiliary agents and vehicles including cyclodextrin clathrates and encapsulation of liposomes.

The active ingredients according to the invention are to be used, in connection with the auxiliary agents known and usual in galenicals, for example, for the production of pharmaceutical agents.

EXAMPLE 1

(5Z,13E,15R)-15-Hydroxy-16-phenoxy-17,18,19,20-tetranor-5,8(9),13-prostatrienoic acid methyl ester The solution of 40 mg (66 micromol) of the compound produced in example 1a is dissolved in 770 microliters of anhydrous tetrahydrofuran, mixed with 151 microliters of a 1M tetrabutylammonium fluoride solution in tetrahydrofuran and allowed to stir for three hours under an atmosphere of dry argon. It is poured on ice water, extracted with diethyl ether, rewashed with a saturated sodium chloride solution and dried on magnesium sulfate. The crude oil obtained after removal of the solvent in the water jet vacuum is purified by chromatography on two analytic thin-layer slabs. A mixture of n-hexane and ethyl acetate is used as a mobile solvent, diethyl ether is used as an eluant. 24 mg (65 micromol, 98%) of the title compound is isolated as a colorless oil.

IR (film): 3600–3200, 3070, 3030, 3010, 2930, 2850, 1735, 1600, 1585, 1495, 1455, 1245, 1080, 1040, 970, 760 and 690 cm$^1$.

EXAMPLE 1a (5Z,13E,15R)-15-t-Butyl-diphenylsilyloxy-16-phenoxy17,18,19,20-tetranor-5,8(9), 13-prostatrienoic acid methyl ester (A) and (5Z,9R,13E,15R)-9-fluoro-15-t-butyl-diphenylsilyloxy-16-phenoxy-17,18,19, 20-tetranor-5,13-prostadienoic acid methyl ester (B)

125 mg (199 micromol) of the compound produced in example 1b is dissolved in 3.6 ml of anhydrous toluene, mixed with 80 microliters of anhydrous pyridine, cooled to $-70°$ C. under an atmosphere of dry argon, mixed with 60 microliters of diethylaminosulfur trifluoride (DAST), allowed to heat slowly to $-30°$ C. and stirred for another 2 hours. It is mixed with a few drops of a saturated sodium bicarbonate solution, allowed to come to room temperature, diluted with water and extracted several times with dichloromethane. It is dried on magnesium sulfate and the crude oil obtained after removal of the solvent in the water jet vacuum is purified by chromatography on 7 analytic thin-layer slabs. An n-hexane-acetone mixture is used as a mobile solvent, diethyl ether is used as an eluant. 40 mg (66 micromol, 33%) of title compound A as well as 47 mg (75 mmol, 38%) of title compound B are isolated.

IR (film) of A: 3070, 3040, 3000, 2940, 2850, 1735, 1600, 1590, 1490, 1450, 1430, 1360, 1300, 1245, 1170, 1110, 1045, 970, 820, 755, 740 and 705 cm$^{-1}$.

IR (film) of B: 3070, 3010, 2950, 2860, 1735, 1600, 1585, 1495, 1450, 1425, 1360, 1245, 1110, 1045, 970, 820, 750, 740 and 705 cm$^{-1}$.

EXAMPLE 1b (5Z,9S,13E,15R)-9-Hydroxy-15-t-butyl-diphenyl-silyloxy-16-phenoxy-17,18,19,20-tetranor-5, 13-prostadienoic acid methyl ester 235 mg of the crude product obtained in example 1c is dissolved in 5 ml of dichloromethane, cooled to 0° to 5° C. and esterified with an ethereal diazomethane solution. After removal of the solvent, the residue is chromatographed on about 30 ml of fine silica gel under pressure. A gradient system of n-hexane and ethyl acetate is used as a mobile solvent. 125 mg (199 micromol, 62% relative to the feedstock in example 1c) is isolated.

IR (film): 3700-3300, 3070, 3040, 3000, 2950, 2930, 2890, 2860, 1735, 1600, 1585, 1495, 1450, 1430, 1245, 1110, 1040, 970, 820, 755, 740 and 705 cm$^{-1}$.

EXAMPLE 1c (5Z,9S,13E,15R) -9-Hydroxy-15-t-butyl-diphenyl-silyloxy-16-phenoxy-17,18,19,20-tetranor-5, 13-prostadienoic acid The solution of 235 mg (321 micromol) of the compound, produced in example 1d, in 1 ml of methanol is mixed with a 5% lithium hydroxide solution and stirred for 5 hours at 25° C. It is poured in ice water, adjusted to a pH of 4 to 5 by adding a saturated citric acid solution, extracted several times with dichloromethane, washed with water and dried on magnesium sulfate. After removal of the solvent, 236 mg of crude product is isolated, which is further reacted without purification.

EXAMPLE 1d (5Z,9S,13E,15R)-9-Benzoyloxy-15-t-butyl-diphenyl-silyloxy-17,18,19,20-tetranor-5, 13-prostadienoic acid methyl ester 309 mg (343 micromol) of the compound produced in example 1e is dissolved in 5 ml of dimethoxyethane, mixed with 519 mg of sodium iodide, 445 mg of zinc dust, 300 microliters of water and heated for 16 hours to 80° C. After the cooling, it is filtered, rewashed with dichloromethane, extracted with water and the organic phase is dried on magnesium sulfate. After removal of the solvent, 238 mg (325 micromol, 95%) of the title compound is isolated as a pale yellow oil.

IR (film): 3070, 3030, 3000, 2950, 2950, 2930, 2860, 1735, 1715, 1600, 1585, 1490, 1450, 1270, 1245, 1110, 970, 820, 750, 740 and 705 cm$^{-1}$.

EXAMPLE 1e (5Z,9S,11R,13E,15R)-9-Benzoyloxy-1-(p-toluenesulfonyloxy)-15-t-butyl-diphenylsilyloxy-16 -phenoxy-17,18,19,20-tetranor-5,13-prostadienoic acid methyl ester 300 mg (402 micromol) of the compound produced in example if is dissolved in 2.7 ml of anhydrous pyridine, mixed with 354 mg of p-toluenesulfonic acid chloride and heated under an atmosphere of dry argon for 7 hours to 50° C. Pyridine is removed by repeated-azeotropic distillation with toluene, the residue is mixed with water and extracted several times with dichloromethane. It is washed with saturated sodium chloride solution, dried on magnesium sulfate and the residue obtained after removal of the solvent in the water jet vacuum is purified by chromatography on about 70 ml of fine silica gel under pressure. A gradient system of n-hexane and ethyl acetate is used as a mobile solvent. 533 mg (591 micromol, 92%) of the title compound is isolated as a colorless oil.

IR (film): 3070, 3040, 3000, 2970, 2930, 2860, 1735, 1715, 1600, 1585, 1495, 1450, 1425, 1360, 1270, 1245, 1175, 1190, 1110, 965, 910, 855, 820, 755, 740, 710 and 665 cm$^{-1}$.

EXAMPLE 1f (5Z,9S,11R,13E,15R)-9-Benzoyloxy-11-hydroxy-15-t-butyl-diphenylsilyloxy-16-phenoxy-17,18,19,20-tetranor-5,13-prostadienoic acid methyl ester 395 mg (475 micromol) of the compound produced in example 1g is reacted analogously to example 5c and, after working up and purification, 327 mg (438 micromol, 92%) of the title compound is isolated as a colorless oil.

IR (film): 3600-3200, 3070, 3040, 3010, 3000, 2950, 2930, 2860, 1735, 1720, 1600, 1585, 1495, 1450, 1430, 1275, 1245, 1175, 1115, 970, 825, 755, 740, 710, 615, 510 and 490 cm$^{-1}$.

EXAMPLE 1g (5Z,9S,11R,13E,15R)-9-Benzoyloxy-11-(tetrahydropyran-2-yloxy)-15-t-butyl-diphenylsilyloxy-16-phenoxy-17,18,19,20-tetranor-5,13-prostadienoic acid methyl ester 3.05 g (5.15 mmol) of the more polar alcohol produced according to example 1h is dissolved in 24 ml of anhydrous dimethylformamide, mixed with 713 mg of imidazole, 2.45 ml of t-butyl-diphenylchlorosilane and stirred for 16 hours at 23° C. under an atmosphere of dry argon. It is poured on ice water, extracted severaltimes with diethyl ether, the combined organic extracts are washed with water and saturated sodium chloride solution, dried on magnesium sulfate and the residue obtained after filtration and removal of the solvent is purified by chromatography on about 250 ml of fine silica gel by a gradient system of n-hexane and ethyl acetate. 3.59 g (4.32 mmol, 84%) of the title compound is isolated as a colorless oil.

IR (film): 3070, 3040, 3010, 2940, 2860, 1735, 1715, 1600, 1585, 1495, 1450, 1425, 1270, 1245, 1110, 1025, 970, 865, 820, 755, 740 and 705 cm$^{-1}$.

EXAMPLE 1h (5Z,9S,11R,13E,15R)-9-Benzoyloxy-11-(tetrahydropyran-2-yloxy)-15-hydroxy-16-phenoxy-17,18,19,20-tetranor-5,13-prostadienoic acid methyl ester (A) and (5Z,9S,11R,13E,15S)-9-benzoyloxy-11-(tetrahydropyran-2-yloxy)-15-hydroxy-16-phenoxy-17,18,19,20-tetranor-5,13-prostadienoic acid methyl ester (B)

7.49 g (12.7 mmol) of the ketone produced in example 1i is reduced analogously to example 9d and, after working up and chromatographic separation, 3.43 g (5.79 mmol, 46%) of title compound B as a more nonpolar component as well as 3.71 g (6.25 mmol, 49%) of title compound A as a more polar component are isolated.

IR (film) of A and B: 3600-3200, 3060, 3010, 2949, 2870, 1735, 1710, 1600, 1495, 1450, 1360, 1275, 1245, 1115, 1070, 1025, 970, 865, 810, 755, 715 and 690 cm$^{-1}$.

EXAMPLE 1i (5Z,9S,11R,13E,15R)-9-Benzoyloxy-11-(tetrahydropyran-2-yloxy)-15-oxo-16-phenoxy-17,18,19,20-tetranor-5,13-prostadienoic acid methyl ester The solution of 7.70 g (16.8 mmol) of (1R,2R,3R,5S)-7-[2-formyl-3-(tetrahydropyran-2-yloxy)-5-benzoyloxycyclopentyl]-5-(Z)-heptenoic acid methyl ester is dissolved in 210 ml of anhydrous dimethoxyethane, mixed with 17.8 g of dimethyl-(2-oxo-3-phenoxy-propyl)-phosphonate lithium salt and stirred for 2 days at 230° C. under an atmosphere of dry argon. It is poured on ice water, extracted several times with diethyl ether, the combined organic extracts are washed with water and saturated sodium chloride-solution, dried on magnesium sulfate and the residue obtained after filtration and removal of the solvent is purified by chromatography on about 600 ml of fine silica gel by a gradient system of n-hexane and ethyl acetate. In addition to 1.59 g of initial material, 7.49 g (12.7 mmol, 75%) of the title compound was isolated as a colorless oil.

IR (film): 3070, 3010, 2950, 2870, 1735, 1715, 1695, 1620, 1600, 1495, 1450, 1275, 1120, 1030, 975, 870, 815, 760, 720 and 695 cm$^{-1}$.

EXAMPLE 2

(5Z,13E,15R)-15-Hydroxy-16-phenoxy-17,18,19,20-tetranor-5,8(9),13-prostatrienoic acid 24 mg (65 micromol) of the compound produced in example 1 is dissolved in 940 microliters of methanol, mixed with 315 microliters of an 8% potassium hydroxide solution and stirred for 5 hours at 25° C. The working up takes place analogously to example 1c. 21 mg (59 micromol, 91%) of the title compound is isolated as a colorless oil.

IR (film): 3600-2400, 3070, 3040, 3010, 2930, 2850, 1710, 1600, 1585, 1495, 1455, 1245, 1080, 1040, 970, 755 and 690 cm$^{-1}$.

EXAMPLE 3

(5Z,13E,15S)-15-Hydroxy-16-phenoxy-17,18,19,20-tetranor-5,8(9),13-prostatrienoic acid methyl ester 42.mg (69 micromol) of the compound produced in example 3a is reacted analogously to example 1 and, after working up and purification, 23 mg (62 micromol, 90%) of the title compound is isolated as a colorless oil.

IR (film): 3600-3200, 3080, 3040, 3010, 2930, 2850, 1740, 1600, 1590, 1500, 1455, 1245, 1080, 1040, 970, 755 and 690 cm$^{-1}$.

EXAMPLE 3a (5Z,13E,15S)-15-t-Butyl-diphenylsilyloxy-16-phenoxy-17,18,19,20-tetranor-5,8(9),13 -prostatrienoic acid methyl ester (A) and (5Z,9R,13E,15S)-9-fluoro-15-t-butyl-diphenylsilyloxy-16-phenoxy-17,18,19, 20-tetranor-5,13-prostadienoic acid methyl ester (B)

103 mg (164 micromol) of the compound produced in example 3b is reacted analogously to example 1a and, after working up and purification, 42 mg (69 micromol, 42%) of title compound A as well as 41 mg (65 micromol, 40%) of title compound B are isolated.

IR (film) of A: 3070, 3040, 3010, 2950, 2930, 2850, 1735, 1600, 1585, 1490, 1425, 1360, 1300, 1240, 1170, 1110, 1040, 970, 820, 750, 740 and 705 cm$^{-1}$.

IR (film) of B: 3070, 3050, 3010, 2950, 2930, 2860, 1735, 1600, 1590, 1495, 1430, 1360, 1245, 1170, 1110, 1045, 970, 820, 755, 740 and 705 cm$^{-1}$.

EXAMPLE 3b (5Z,9S,13E,15S)-9-Hydroxy-15-t-butyl-diphenylsilyloxy-16-phenoxy-17,18,19,20-tetranor-5, 13-prostadienoic acid methyl ester 420 mg of the crude product produced in example 3c is reacted analogously to example 1b and, after working up and purification, 233 mg (372 micromol, 67% relative to the feedstock in example 3c) of the title compound is isolated as a colorless oil.

IR (film): 3600-3300, 3070, 3040, 3000, 2950, 2950, 2930, 2860, 1735, 1600, 1590, 1495, 1425, 1240, 1110, 1040, 970, 820, 755, 740 and 705 cm$^{-1}$.

EXAMPLE 3c p (5Z,9S,13E,15S)-9-Hydroxy-15-t-butyl-diphenylsilyloxy-16-phenoxy-17,18,19, 20-tetranor-5,13-prostadienoic acid 406 mg (555 micromol) of the compound produced in example 3d is reacted analogously to example 1c and, after working up, 432 mg of crude product is isolated, which is further reacted without purification.

EXAMPLE 3d (5Z,9S,13E,15S)-9-Benzoyloxy-15-t-butyl-diphenylsilyloxy-16-phenoxy-17,18,19,20-tetranor-5,13-prostadienoic acid methyl ester 533 mg (591 micromol) of the compound produced in example 3e is reacted analogously to example 1d and, after working up and purification, 401 mg (576 micromol, 97%) of the title compound is isolated as a pale yellow oil.

IR (film): 3070, 3040, 3000, 2950, 2930, 2860, 1735, 1710, 1600, 1585, 1490, 1450, 1430, 1270, 1245, 1110, 970, 820, 750, 740 and 705 cm$^{-1}$.

EXAMPLE 3e (5Z,9S,11R,13E,15S)-9-Benzoyloxy-11-(p-toluenesulfonyloxy)-15-t-butyl-diphenylsilyloxy-16-17,18,19,20-tetranor-5,13-prostadienoic acid methyl ester 479 mg (641 micromol) of the compound produced in example 3f is reacted analogously to example 1e and, after working up and purification, 533 mg (591 micromol, 92%) of the title compound is isolated as a colorless oil.

IR (film): 3070, 3040, 2940, 2860, 1720 (broad), 1600, 1495, 1450, 1430, 1360, 1270, 1245, 1175, 1110, 970, 910, 850, 820, 750, 710 and 665 cm$^{-1}$.

EXAMPLE 3f (5Z,9S,11R,13E,15S)-9-Benzoyloxy-11-hydroxy-15-t-butyl-diphenylsilyloxy-16-phenoxy-17,18,19,20-tetranor-5,13-prostadienoic acid methyl ester 960 mg (1.16 mmol) of the compound produced in example 3g is reacted analogously to example 5c and, after working up and purification, 607 mg (813 micromol, 70%) of the title compound is isolated as a colorless oil.

IR (film): 3600-3200, 3070, 3040, 3010, 3000, 2950, 2930, 2860, 1735, 1715, 1600, 1585, 1495, 1450, 1425, 1360, 1315, 1275, 1245, 1175, 1115, 970, 825, 755, 740, 705, 690, 615, 510 and 490 cm$^{-1}$.

EXAMPLE 3g (5Z,9S,11R,13E,15S)-9-Benzoyloxy-11-(tetrahydropyran-2-yloxy)-15-t-butyl-diphenylsilyloxy-16-phenoxy-17,18,19,20-tetranor-5,13-prostadienoic acid methyl ester 2.77 g (4.67 mmol) of the more nonpolar alcohol produced in example 1h is silylated analogously to example 1g and, after working up and purification, 3.31 g (3.98 mmol, 85%) of the title compound is isolated as a colorless oil.

IR (film): 3070, 3050, 3010, 2940, 2860, 1735, 1715, 1600, 1585, 1450, 1430, 1270, 1245, 1110, 1025, 970, 860, 820, 740 and 705 cm$^{-1}$.

EXAMPLE 4

(5Z,13E,15S)-15-Hydroxy-16-phenoxy-17,18,19,20-tetranor-5,8(9),13-prostatrienoic acid 23.mg (62 micromol) of the compound produced in example 3 is reacted analogously to example 2 and, after working up, 19.8 mg (56 micromol, 89%) of the title compound is isolated as a colorless oil.

IR (film): 3600-2400, 3070, 3040, 3010, 2930, 2850, 1710, 1600, 1590, 1500, 1460, 1245, 1080, 1040, 970, 755 and 690 cm$^{-1}$.

EXAMPLE 5

(5Z,11S,13E,15R)-11,15-Dihydroxy-16-phenoxy-17,18,19,20-tetranor-5, 8(9),13-prostatrienoic acid 20 mg (41 micromol) of the compound produced in example 5a is saponified analogously to example 1c and, after working up and purification, 14 mg (78 micromol, 92%) of the title compound is isolated as a colorless oil.

IR (film): 3600-2500, 3050, 3010, 2930, 2870, 1710, 1600, 1585, 1495, 1245, 1080, 1040, 975, 810, 755 and 690 cm$^{-1}$.

EXAMPLE 5a (5Z,11S,13E,15R)-11-Benzoyloxy-15-hydroxy-16-phenoxy-17,18,19,20-tetranor-5, 8(9),13-prostatrienoic acid methyl ester 33 mg (45 micromol) of the compound produced in example 5b is reacted analogously to example 1 and, after working up and purification, 20 mg (41 micromol, 90%) of the title compound is isolated as a colorless oil.

IR (film): 3600-3200, 3060, 3010, 2950, 2870, 1735, 1710, 1600, 1495, 1450, 1360, 1245, 1110, 1070, 1025, 970, 755, 715 and 695 cm$^{-1}$.

EXAMPLE 5b (5Z,11S,13E,15R)-11-Benzoyloxy-15-t-butyl-diphenylsilyloxy-16-phenoxy-17,18,19, 20-tetranor-5,8(0),13-prostatrienoic acid methyl ester 38 mg (61 micromol) of the compound produced in example 5c is dissolved in 1.5 ml of anhydrous toluene, mixed with 35 mg of triphenylphosphine, 16.4 mg of benzoic acid with 21 microliters of azodicarboxylic acid diethyl ester (DEAD). It is stirred for 3 hours at 25° C. under an atmosphere of dry argon, mixed with water, extracted several times with diethyl ether, dried on magnesium sulfate and the residue obtained after removal of the solvent is purified by chromatography on 7 analytic thin-layer slabs. A mixture of ethyl acetate and n-hexane is used as a mobile solvent, ethyl acetate is used as an eluant. 33 mg (45 micromol, 74%) of the title compound is isolated as a colorless oil.

IR (film): 3070, 3030, 3000, 2950, 2930, 2860, 1735, 1715, 1600, 1590, 1490, 1490, 1450, 1425, 1270, 1245, 1110, 970, 820, 750 and 705 cm$^{-1}$.

EXAMPLE 5c (5Z,11R,13E,15R)-11-Hydroxy-15-t-butyl-diphenyl-silyloxy-16-phenoxy-17,18,19, 20-tetranor-5,8(9),13-prostadienoic acid methyl ester 69 mg (97 micromol) of the compound produced in example 5d is dissolved in 1.5 ml of methanol, mixed with 8 mg of pyridinium-p-toluenesulfonate (PPTs) and heated under an atmosphere of dry argon for 2 hours to 55° C. After cooling, it is mixed with dichloromethane, washed with water and saturated sodium chloride solution, dried on magnesium sulfate and the residue obtained after removal of the solvent is purified by chromatography on 3 analytic thin-layer slabs. A mixture of ethyl acetate and n-hexane is used as a mobile solvent, ethyl acetate is used as an eluant. 38 mg (61 micromol, 62%) of the title compound is isolated as a colorless oil.

IR (film): 3600-3200, 3070, 3030, 3000, 2940, 2860, 1735, 1600, 1585, 1495, 1450, 1245, 1110, 1040, 970, 815, 755, 740 and 705 cm$^{-1}$.

EXAMPLE 5d (5Z,11R,13E,15R)-11-(Tetrahydropyran-2-yloxy)-15-t-butyl-diphenylsilyloxy-16-phenoxy-17, 18,19,20-tetranor-5,8(9),13-prostadienoic methyl ester (A) and (5Z,9R,11R,13E,15R)-9-fluoro-11-(tetrahydropyran-2-yloxy)-15-t-butyl-diphenylsilyloxy-16-phenoxy-17,18,19,20-tetranor-5,8(9),13-prostadienoic acid methyl ester (B)

213 mg (293 micromol) of the compound produced in example 5e is reacted analogously to example 1a and, after working up and purification, 80 mg (113 micromol, 39%) of title compound A as well as 91 mg (125 micromol, 43%) of title compound B are isolated.

IR (film) of A: 3070, 3040, 3010, 2940, 2860, 1735, 1600, 1595, 1490, 1450, 1425, 1355, 1245, 1110, 1045, 970, 870, 820, 755, 740 and 705 cm$^{-1}$.

IR (film) of B: 3060, 3030, 3000, 2950, 2860, 1735, 1600, 1590, 1495, 1450, 1425, 1360, 1245, 1110, 1045, 970, 865, 820, 750, 740 and 705 cm$^{-1}$.

EXAMPLE 5e (5Z,9S,11R,13E,15R)-9-Hydroxy-11-(tetrahydropyran-2-yloxy)-15-t-butyl-diphenylsilyloxy-16-phenoxy-17,18,19,20-tetranor-5,13-prostadienoic acid methyl ester 1.49 g (1.79 mmol) of the compound produced according to example 1g is reacted analogously to example 1c and 1b and, after working up and purification, 1.14 g (1.57 mmol, 88%) of the title compound is isolated as a colorless oil.

IR (film): 3600-3200, 3070, 3040, 3000, 2960, 2940, 2860, 1735, 1600, 1585, 1495, 1245, 1110, 1040, 970, 865, 820, 755, 740 and 705 cm$^{-1}$.

EXAMPLE 6

(5Z,11S,13E,15R)-11,15-Dihydroxy-16-phenoxy-17,18,19,20-tetranor-5,8(9), 13-prostatrienoic acid methyl ester 6.7 mg (18 micromol) of the compound produced in example 5 is esterified analogously to example 1b and, after removal of the solvent, 6.5 mg (17 micromol, 93%) of the title compound is isolated as a colorless oil.

IR (film): 3600-3200, 3080, 3010, 2940, 2870, 1735, 1600, 1590, 1495, 1245, 1080, 1040, 970, 810, 755 and 690 cm$^{-1}$.

EXAMPLE 7

(5Z,11S,13E,15S)-11-Dihydroxy-16-phenoxy-17,18,19, 20-tetranor-5,8(9),13-prostatrienoic acid 109 mg (222 micromol) of the compound produced in example 7a is saponified analogously to example 1c and after working up and chromatographic purification, 65 mg (175 micromol, 79%) of the title compound is isolated as a colorless oil.

IR (film): 3600-2500, 3070, 3050, 3020, 2940, 2870, 1710, 1600, 1590, 1500, 1245, 1080, 755 and 695 cm$^{-1}$.

EXAMPLE 7a (5Z,11S,13E,15S)-11-Benzoyloxy-15-hydroxy-16-phenoxy-17,18,19, 20-tetranor-5,8(9),13-prostatrienoic acid methyl ester (A) and (5Z,9R,11S,13E,15S)-9-fluoro-11-benzoyloxy-15-hydroxy-16-phenoxy-17,18,19, 20-tetranor-5,13-prostadienoic acid methyl ester 355 mg (about 500 micromol) of the mixture produced in example 7b is reacted analogously to example 1 and, after working up and chromatographic purification, 109 mg (222 micromol, 36% relative to the feedstock in example 7d) of title compound A as well as 139 mg (273 micromol, 45% relative to the feedstock in example 7d) of title compound B are isolated.

IR (film) of A and B: 3600-3200, 3050, 3010, 2950, 2870, 1735, 1710, 1600, 1495, 1450, 1245, 1110, 1065, 970, 755, 715 and 695 cm$^{-1}$.

EXAMPLE 7b (5Z,11S,13E,15S)-11-Benzoyloxy-15-t-butyl-diphenylsilyloxy-16-phenoxy-17,18,19, 20-tetranor-5,8(9),13-prostatrienoic acid methyl ester and (5Z,9R,11S,13E,15S)-9-fluoro-11-benzoyloxy-15-t-butyl-diphenylsilyloxy-16, 17,18,19,20-tetranor-5,13prostadienoic acid methyl ester 350 mg (about 550 micromol) of the mixture produced in example 7c is reacted analogously to example 5b and, after working up and purification, 359 mg (about 500 micromol, 91%) of a mixture of both title compounds is isolated, which is further reacted without separation.

IR (film): 3070, 3050, 3010, 2950, 2860, 1735, 1710, 1600, 1595, 1495, 1425, 1360, 1245, 1170, 1100, 1040, 970, 820, 755, 740 and 705 cm$^{-1}$.

EXAMPLE 7c (5Z,11R,13E,15S)-11-Hydroxy-15-t-butyl-diphenylsilyloxy-16-phenoxy-17,18,19, 20-tetranor-5,8(9),13-prostatrienoic acid methyl ester and (5Z,9R,11R,13E,15S)-9-fluoro-11-hydroxy-15-t-butyl-diphenylsilyloxy-16-phenoxy-17,18,19,20-tetranor-5,13prostadienoic acid methyl ester 389 mg (about 550 micromol) of the mixture produced in example 7d is reacted analogously to example 5c and, after working up and purification, 350 mg (about 550 micromol, about 100%) of a mixture of both title compounds is isolated, which is further reacted without separation.

IR (film): 3600-3200, 3070, 3030, 3010, 2950, 2870, 1735, 1600, 1590, 1495, 1450, 1245, 1110, 1035, 970, 820, 755, 740 and 705 cm$^{-1}$.

EXAMPLE 7d (5Z,11R,13E,15S)-11-(Tetrahydropyran-2-yloxy)-15-t-butyl-diphenylsilyloxy-16-phenoxy-17,18,19,20-tetranor-5,8(9),13prostatrienoic acid methyl ester and (5Z,9R,11R,13E,15S)-9-fluoro-11-(tetrahydropyran-2-yloxy)-15-t-butyl-diphenylsilyloxy-16-phenoxy-17,18,19,20-tetranor-5,13-prostadienoic acid methyl ester 434 mg (609 micromol) of the compound produced in example 7e is reacted analogously to example 1a and, after working up and purification, 389 mg (about 540 micromol, about 88%) of a mixture of both title compounds is isolated, which is further reacted without separation.

IR (film): 3080, 3040, 3010, 2950, 2860, 1730, 1600, 1595, 1495, 1450, 1425, 1355, 1245, 1110, 1045, 970, 865, 820, 755, 740 and 705 cm$^{-1}$.

EXAMPLE 7e (5Z,9S,11R,13E,15S)-9-Hydroxy-11-(tetrahydropyran-2-yloxy)-15-t-butyl-diphenylsilyloxy-16-phenoxy-17,18,19,20-tetranor-5,13-prostadienoic acid methyl ester 755 mg (908 micromol) of the compound produced according to example 3g is reacted analogously to examples 1c and 1b and, after working up and purification, 523 mg (719 micromol, 79%) of the title compound is isolated as a colorless oil.

IR (film): 3600-3200, 3070, 3040, 3010, 2960, 2850, 1735, 1600, 1585, 1495, 1245, 1110, 1040, 970, 870, 820, 755, 740 and 705 cm$^{-1}$.

EXAMPLE 8

(5Z,11S,13E,15S)-11,15-Dihydroxy-16-phenoxy-17,18,19,20-tetranor-5,8(9), 13-prostatrienoic acid methyl ester 11 mg (30 micromol) of the compound produced in example 7 is esterified analogously to example 1b and, after working up and purification, 10 mg (26 micromol, 88%) of the title compound is isolated as a colorless oil.

IR (film): 3600-3300, 3070, 3050, 3010, 2940, 2870, 1740, 1600, 1590, 1500, 1245, 1080, 1040, 755 and 695 cm$^{-1}$.

EXAMPLE 9

(5Z,11R,13E,15R)-11,15-Dihydroxy-17-phenoxy-17,18,19,20-trinor-5,8(9), 13-prostatrienoic acid methyl ester 316 mg (572 micromol) of compound A produced in example 9a is mixed with 14 ml of a glacial acetic acid:water:tetrahydrofuran (65:35:10) mixture and allowed to stir for 16 hours at 23° C. It is concentrated by evaporation in the water jet vacuum and residual acetic acid is removed azeotropically by repeated addition of toluene. 214 mg (556 micromol, 97%) of the title compound is isolated as a colorless oil, which is further reacted without purification.

IR (film): 3600-3200, 3070, 3060, 3020, 2940, 2870, 1735, 1600, 1495, 1450, 1410, 1245, 1035, 970, 750 and 700 cm$^{-1}$.

EXAMPLE 9a (5Z,11R,13E,15R)-11,15-bis-(Tetrahydropyran-2-yloxy)17-phenyl-18,19,20-trinor-5, 8(9),13-prostatrienoic acid methyl ester (A) and (5Z,9R,11R,13E,15R)9-fluoro-11,15-bis-(tetrahydropyran-yloxy)-17-phenyl-18,19, 20-trinor-5,13-prostadienoic acid methyl ester (B) 1.24 g (2.18 mmol) of the compound produced in example 9b is reacted analogously to example 1a and, after working up and purification, 316 mg (572 micromol, 26%) of title compound A as well as 360 mg (629 micromol, 29%) of title compound (B) are isolated.

IR (film) of A: 3060, 3030, 2950, 2870, 1740, 1605, 1455, 1440, 1200, 1200, 1135, 1120, 1080, 1030, 980, 870, 815, 750 and 700 cm$^{-1}$.

IR (film) of B: 3090, 3070, 3030, 3010, 2940, 2870, 1740, 1455, 1440, 1355, 1075, 1030, 975, 870, 815, 750 and 700 cm$^{-1}$.

EXAMPLE 9b (5Z,9S,11R,13E,15R)-9-Hydroxy-11,15-bis-(tetrahydropyran-2-yloxy)-17-phenyl-18,19, 20-trinor-5,13-prostadienoic acid methyl ester 1.51 g (2.24 mmol) of the compound produced in example 9c is dissolved in 50 ml of anhydrous methanol, mixed with 0.66 g of finely pulverized potassium carbonate and stirred for 60 hours at 23° C. under an atmosphere of dry argon. It is diluted with water, extracted several times with diethyl ether, the combined organic extracts are washed with water and saturated sodium chloride solution, dried on magnesium sulfate and the residue obtained after removal of the solvent is purified by chromatography on about 100 ml of fine silica gel with a mobile solvent mixture of n-hexane and ethyl acetate. 1.24 g (2.18 mmol, 91%) of the title compound is isolated as a colorless oil.

IR (film): 3600-3200, 3090, 3060, 3030, 3010, 2950, 2870, 1740, 1600, 1455, 2440, 1250, 1135, 1080, 1025, 980, 870, 815, 750 and 705 cm$^{-1}$.

EXAMPLE 9c (5Z,9S,11R,13E,15R)-9-Benzoyloxy-11,15-bis-(tetrahydropyran-2-yloxy)-17-phenyl-18, 19,20-trinor-5,13-prostadienoic acid methyl ester The solution of 1.41 g (2.3 mmol) of compound B, produced in example 9d, in 50 ml of anhydrous dichloromethane is mixed with 6 mg of p-toluenesulfonic acid and 260 microliters of dihydropyran. It is allowed to stir for 1 hour at 23° C. under an atmosphere of dry argon, the violet-colored solution is mixed with 25 ml of a 10% sodium bicarbonate solution, the organic phase is separated, rewashed several times with water and dried on magnesium sulfate. After filtration and removal of the solvent in the water Set vacuum, 1.77 g of a yellow oil, which is chromatographically purified on about 100 ml of fine silica gel by a mixture of n-hexane and ethyl acetate. 1.51 g (2.24 mmol, 97%) of the title compound is isolated as a colorless oil.

IR (film): 3090, 3060, 3030, 3010, 2940, 2870, 1740, 1600, 1585, 1450, 1440, 1350, 1275, 1130, 1115, 1025, 975, 870, 815, 750 and 700 cm$^{-1}$.

EXAMPLE 9d (5Z,9S,11R,13E,15S)-9-Benzoyloxy-11-(tetrahydropyran-2-yloxy)-15-hydroxy-17-phenyl-18,19,20-trinor-5,13 -prostadienoic acid methyl ester (A) and (5Z,9S,11R,13E,15R)-9-benzoyloxy-11-(tetrahydropyran-2-yloxy) -15-hydroxy-17-phenyl-18,19,20-trinor-5,13-prostadienoic acid methyl ester (B)

3.43 g (5.882 mmol) of the unsaturated ketone produced in example 9e is dissolved in 68 ml of methanol, cooled under an atmosphere of dry argon to −40° C. and mixed with 1.39 g of sodium borohydride. After one hour, it is quenched by adding 3 ml of glacial acetic acid, allowed to heat to room temperature and extracted several times with diethyl ether. It is dried on magnesium sulfate and the residue obtained after removal of the solvent is purified by chromatography on about 150 g of fine silica gel. A mixture of n-hexane and ethyl acetate is used as an eluant. 1.41 g (2.3 mmol, 41%) of a nonpolar component, to which structure B is assigned, in addition to 1.11 g (1.88 mmol, 32%) of a more polar component, to which structure A is assigned, are isolated.

IR (film) of A: 3600-3200, 3090, 3070, 3030, 3010, 2950, 2870, 1735, 1720, 1600, 1585, 1445, 1440, 1355, 1315, 1275, 1120, 1075, 1030, 975, 870, 810, 750, 720 and 705 cm$^{-1}$.

IR (film) of B: 3600-3200, 3090, 3070, 3030, 3010, 2950, 2860, 1735, 1720, 1600, 1580, 1440, 1435, 1315, 1275, 1120, 1075, 1030, 975, 870, 815, 750, 715 and 705 cm$^{-1}$.

EXAMPLE 9e (5Z,9S,11R,13E)-9-Benzoyloxy-11-(tetrahydropyran-2-yloxy)-15-oxo-17-phenyl-18,19, 20-trinor-5,13-prostadienoic acid methyl ester The solution of 513 mg of dimethyl-(2-oxo-4-phenylbutyl)-phosphonate in 3 ml of acetonitrile is added to the mixture of 85 mg of anhydrous lithium chloride in 20 ml of anhydrous acetonitrile under an atmosphere of dry argon, mixed with 140 microliters of DBU and then with the solution of 458 mg (1.00 mmol) of (1R,2R,3R,5S)-7-[2-formyl-3-(tetrahydropyran-2-yloxy)-5-benzoyloxycyclopentyl]-5(Z)-heptenoic acid methyl ester in 4 ml of acetonitrile and allowed to stir for 17 hours at 23° C. It is diluted with methyl-t-butyl ether, filtered, the filtrate is washed with water and saturated sodium chloride solution and dried on magnesium sulfate. The crude product obtained after removal of the solvent is purified by chromatography on about 50 ml of fine silica gel with use of a mixture of n-hexane and ethyl acetate. 567 mg (963 micromol, 96%) of the title compound is isolated as a colorless oil.

IR (film): 3090, 3060, 3030, 3010, 2950, 2870, 1735, 1720, 1675, 1630, 1605 and 700 cm$^{-1}$.

EXAMPLE 10

(5Z,11R,13E,15R)-11,15-Dihydroxy-17-phenyl-18,19,20-trinor-5,8(9),13-prostatrienoic acid 214 mg (556 micromol) of the compound produced in example 9 is reacted analogously to example 2 and, after working up, 95 mg (256 micromol, 46%) of the title compound is isolated as a colorless oil.

IR (film): 3600-2400, 3080, 3060, 3020, 2930, 2880, 1710, 1600, 1495, 1450, 1410, 1240, 1030, 970, 750 and 700 cm$^{-1}$.

EXAMPLE 11

(5Z,11R,13E,15S)-11,15-Dihydroxy-17-phenyl-18,19,20-trinor-5,8(9),13-prostatrienoic acid methyl ester 247 mg (447 micromol) of compound A produced in example 11a is reacted analogously to example 9 and, after working up and purification, 165 mg (428 micromol, 96%) of the title compound is isolated as a colorless oil.

IR (film): 3600-3200, 3080, 3060, 3030, 2940, 2860, 1740, 1605, 1500, 1455, 1245, 1050, 970, 750 and 695 cm$^{-1}$.

(5Z,11R,13E,15S)-11,15-bis-(Tetrahydropyran-2-yloxy)-17-phenyl-18, 19,20-trinor-5,8(9),13-prostadienoic acid methyl ester (A) and (5Z,9R,11R,13E,15S)-9-fluoro-11,15-bis-(tetrahydropyran-2-yloxy)-17-phenyl-18,19,20-trinor-5,13-prostadienoic acid methyl ester (B)

816 mg (1.43 mmol) of the compound produced in example 11b is reacted analogously to example 1a and, after working up and purification, 247 mg (447 micromol, 31%) of title compound A as well as 314 mg (549 micromol, 38%) of title compound (B) are isolated.

IR (film) of A: 3090, 3060, 3020, 2940, 2850, 2830, 1740, 1605, 1440, 1355, 1205, 1135, 1120, 1080, 1030, 980, 750 and 705 cm$^{-1}$.

IR (film) of B: 3090, 3060, 3010, 2950, 2870, 1740, 1605, 1500, 1455, 1440, 1365, 1355, 1200, 1135, 1080, 1020, 870, 820, 750 and 700 cm$^{-1}$.

EXAMPLE 11b (5Z,9S,11R,13E,15S)-9-Hydroxy-11,15-bis-(tetrahydropyran-2-yloxy)-17-phenyl-18,19,20-trinor-5,13-prostadienoic acid methyl ester 1.12 mg (1.66 mmol) of the compound produced in example 11c is reacted analogously to example 9b and, after working up and purification, 816 mg (1.43 mmol, 86%) of the title compound is isolated as a colorless oil.

IR (film): 3600-3200, 3090, 3060, 3010, 2950, 2870, 1735, 1605, 1445, 1440, 1200, 1135, 1115, 1080, 1025, 975, 870, 815, 750 and 700 cm$^{-1}$.

EXAMPLE 11c (5Z,9S,11R,13E,15S)-9-Benzoyloxy-11,15-bis-(tetrahydropyran-2-yloxy)-17-phenyl-18,19,20-trinor-5,13-prostadienoic acid methyl ester 1.11 g (1.88 mmol) of the compound produced in example 9d is reacted analogously to example 9c and, after working up and purification, 1.12 g (1.66 mmol, 88%) of the title compound is isolated as a colorless oil.

IR (film): 3090, 3060, 3030, 3010, 2940, 2870, 1740, 1720, 1600, 1585, 1450, 1440, 1355, 1315, 1375, 1120, 1025, 970, 870, 810, 750, 710 and 700 cm$^{-1}$.

EXAMPLE 12

(5Z,11R,13E,15S)-11,15-Dihydroxy-17-phenyl-18,19,20-trinor-5, 8(9),13-prostatrienoic acid 165 mg (428 micromol) of the compound produced in example 11 is reacted analogously to example 2 and, after working up, 63 mg (170 micromol, 40%) of the title compound is isolated as a colorless oil.

IR (film): 3600-2400, 3090, 3060, 3030, 2930, 2860, 1710, 1605, 1500, 1455, 1410, 1245, 1050, 975, 750 and 700 cm$^{-1}$.

We claim:

1. $\Delta^8$-prostaglandin derivatives of formula I,

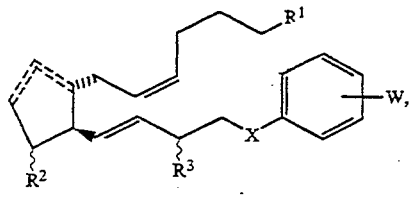

in which ⌒ means the radicals ⌒ or ⌒, $R^1$ can be

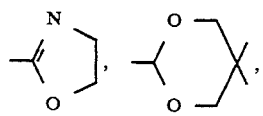

$COOR^4$, in which $R^4$ can mean hydrogen or a $C_1$-$C_{10}$ alkyl radical optionally substituted by halogen, phenyl, $C_1$-$C_4$ alkoxy or di-($C_1$-$C_4$) alkylamino, a $C_3$-$C_{10}$ cycloalkyl radical, a $C_7$-$C_{16}$aralkyl radical, a phenaryl radical substituted by W, a $C_6$-$C_{12}$ aryl radical or a 5- or 6-member heterocyclic radical with at least one N, O or S atom, or $R^1$ can be a $CONHR^5$ radical with $R^5$ meaning hydrogen, $C_1$-$C_{10}$ alkanoyl or $C_1$-$C_{10}$ alkanesulfonyl, $R^2$ and $R^3$ respectively mean a (1) hydrogen atom or (2) a free or functionally modified hydroxy group, said compound being 11S-hydroxy, X means a $CH_2$ group, an O or S atom, W means hydrogen, $-OR^6$, halogen, $-CN-$, $-NO_2$, trifluoromethyl or $COOR^6$ $R^6$ can be hydrogen, $C_1$-$C_{10}$ alkyl, $C_6$-$C_{12}$ aryl or $C_7$-$C_{16}$ aralkyl substituted by halogen, or if $R^4$ means hydrogen, their salts with physiologically compatible bases, the alpha-, beta- or gamma-cyclodextrin clathrates, or the compounds of formula I encapsulated with liposomes.

2. $\Delta^8$-Prostaglandin derivatives of formula I according to claim 1, characterized in that $R^1$ means the radical $COOR^4$ with $R^4$ as hydrogen or $C_1$-$C_6$ alkyl or $R^1$ means the radical $CONHR^5$ with $R^5$ as methylsulfonyl, X means a $CH_2$ group or an O atom, $R^2$ and $R^3$ mean hydrogen or hydroxy and W means hydrogen or fluorine.

3. Pharmaceutical agents of one or more compounds according to claim 1 and usual auxiliary agents, vehicles and additives.

4. A process for characterization of prostaglandin receptors and $TXA_2/PGH_2$ receptor subtypes comprising measuring the receptor binding by administering an effective amount of a $\Delta^8$- prostaglandin derivative of formula I according to claim 1 as a diagnostic auxiliary agent.

5. A process for the production of $\Delta^{8,9}$-prostaglandin compounds of formula I',

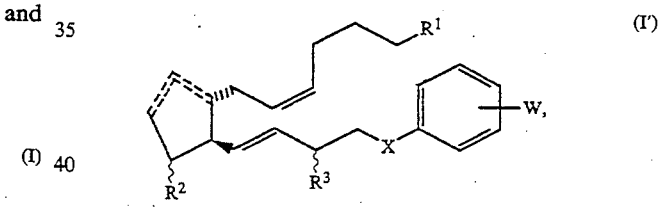

in which ⌒ means the radicals ⌒ or ⌒, $R^1$ can be

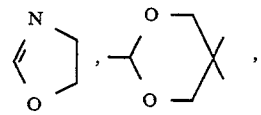

$COOR^4$, in which $R^4$ can mean hydrogen or a $C_1$-$C_{10}$ alkyl radical optionally substituted by halogen, phenyl, $C_1$-$C_4$ alkoxy or di-($C_1$-$C_4$) alkylamino, a $C_3$-$C_{10}$ cycloalkyl radical, a $C_7$-$C_{16}$aralkyl radical, a phenaryl radical substituted by W, a $C_6$-$C_{12}$ aryl radical or a 5- or 6-member heterocyclic radical with at least one N, O or S atom, or $R^1$ can be a $CONHR^5$ radical with $R^5$ meaning hydrogen, $C_1$-$C_{10}$ alkanoyl or $C_1$-$C_{10}$ alkanesulfonyl, $R^2$ and $R^3$ respectively means a (1) hydrogen atom or (2) a free or functionally modified hydroxy group, X means a $CH_2$ group, an O or S atom, W means hydrogen, $-OR^6$, halogen, $-CN-$, $-NO_2$, trifluoromethyl or $COOR^6$ $R^6$ can be hydrogen, $C_1$–$C_{10}$ alkyl, $C_6$–$C_{12}$ aryl or $C_7$–$C_{16}$ aralkyl substituted by halogen, or if $R^4$ means hydrogen, their salts with physiologically compatible bases, the alpha-, beta- or gamma-cyclodextrin clathrates, or the compounds of formula I encapsulated with liposomes, wherein a compound of formula II

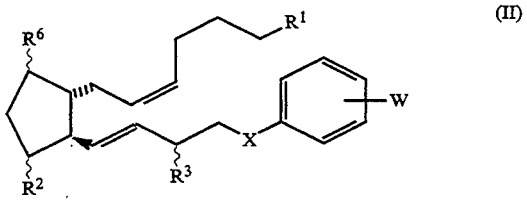

in which $R^4$ exhibits a hydroxy group and $R^1$, $R^2$, $R^3$, X and W have the above-indicated meanings and free OH groups in $R^2$, $R^3$ and W are protected, is reacted with diethylaminosulfur trifluoride, $(HF)_n$-pyridine or $SeF_4$-pyridine and protected hydroxy groups in $R^2$, $R^3$ and W are released and/or free hydroxy groups are esterified, etherified, and/or an esterified carboxy group is saponified or a carboxyl group with a physiologically compatible base is converted to a salt or reacted to a clathrate with alpha-, beta- or gamma-cyclodextrin or encapsulated with liposomes, and separating and recovering a mixture of $\Delta^{8,9}$-prostaglandin compounds of formula I'.

* * * * *

UNITED STATES PATENT AND TRADEMARK OFFICE
CERTIFICATE OF CORRECTION

PATENT NO. : 5,376,683
DATED : December 27, 1994
INVENTOR(S) : Ulrich KLAR et al.

It is certified that error appears in the above-indentified patent and that said Letters Patent is hereby corrected as shown below:

Title Page, Item (63) Related U.S. Application Data:

Change 1992 to read - - 1991 - - .

Signed and Sealed this

Twenty-fifth Day of April, 1995

Attest:

BRUCE LEHMAN

*Attesting Officer*          *Commissioner of Patents and Trademarks*